United States Patent [19]

Sanchez

[11] Patent Number: 5,028,737
[45] Date of Patent: Jul. 2, 1991

[54] PREPARATION OF ISOPROPYLIDENE BIS(PHTHALIC ACID)

[75] Inventor: Paul A. Sanchez, Lisle, Ill.

[73] Assignee: Amoco Corporation, Chicago, Ill.

[21] Appl. No.: 484,346

[22] Filed: Feb. 22, 1990

[51] Int. Cl.$^5$ .......................................... C07C 51/265
[52] U.S. Cl. .................................. 562/416; 502/169;
  502/170; 562/412; 562/417
[58] Field of Search ....................... 562/412, 416, 417;
  502/169, 170, 227, 324, 325, 349

[56] References Cited

U.S. PATENT DOCUMENTS

| | | | |
|---|---|---|---|
| 3,920,735 | 11/1975 | Wampfler et al. | 562/412 |
| 4,314,073 | 2/1982 | Crooks | 562/416 |
| 4,786,621 | 11/1988 | Holzhauer et al. | 502/28 |
| 4,786,753 | 11/1988 | Partenheimer et al. | 562/416 |

*Primary Examiner*—Jose G. Dees
*Assistant Examiner*—Vera C. Clarke
*Attorney, Agent, or Firm*—Thomas E. Nemo; William H. Magidson; Ralph C. Medhurst

[57] ABSTRACT

An oxidation process is provided for converting dixylylpropane to isopropylidene bis(phthalic acid) in good yields with minimal by-product production, especially trimellitic acid production. The oxidation process employs an oxidation catalyst that includes zirconium as well as cobalt, manganese, and bromine.

11 Claims, No Drawings

PREPARATION OF ISOPROPYLIDENE BIS(PHTHALIC ACID)

FIELD OF THE INVENTION

This invention relates to the preparation of isopropylidene bis(phthalic acid).

BACKGROUND OF INVENTION

Isopropylidene bis(phthalic acid), also known as 2,2-bis-(3,4-dicarboxyphenyl)propane (IBPA), is a useful chemical intermediate. For example, this tetracarboxylic acid can be dehydrated to produce isopropylidene bis(phthalic anhydride) (IPAN) from which polymers with enhanced blending properties in polyether ketone formulations can be prepared. Alternatively, the dianhydride can be converted to an ester which can then be used in the manufacture of polyimide resin having a reduced dielectric constant and useful in electronic composites.

Oxidation processes for producing IBPA from dixylylpropane (DXP), also known as isopropylidene bis(xylene) and as 2,2-bis-(3,4-dimethylphenyl)propane, have previously been described in, for example, Gresham et al. U.S. Pat. No. 2,712,543 where nitric acid and also potassium permanganate oxidation of DXP to IBPA are taught. However, both these oxidation processes consume relatively large amounts of inorganic reagents, involve elaborate procedures, and produce IBPA yields of questionable economic value, as well as a relatively large number of undesired by-products.

A possibly more promising oxidative route for preparing IBPA from DXP would be to utilize an alkyl aromatic oxidation process such as the so-called "Mid-Century Oxidation Process" generally described by Towle et al., "Make Most Aromatic Acids Using Mid-Century Oxidation Processes", in *Petrochemical Developments*, November, 1964, Vol. 43, No. 11, pp. 149–152. See also Baldwin U.S. Pat. No. 3,064,044, Marsh et al. U.S. Pat. No. 4,081,464, and Brown et al. U.S. Pat. No. 4,587,355. However, liquid phase, elevated temperature oxidation of DXP using a cobalt-/manganese/bromine catalyst as in the Mid-Century oxidation process is not very efficient for the manufacture of IBPA. Relatively low yields of IBPA are obtained, and unacceptably high amounts of an unwanted by-product, trimellitic acid, are produced.

A new and improved oxidation process for converting DXP to IBPA would be economically advantageous. The present invention provides such a process.

SUMMARY OF THE INVENTION

Dixylylpropane is oxidized to isopropylidene bis(phthalic acid) in relatively high yields using a liquid phase oxidation process and an oxidation catalyst system that includes zirconium. As compared to prior art oxidation processes, in the present process the amount of by-products, especially of trimellitic acid (TMA), is substantially reduced.

The oxidation catalyst system contemplated by the present invention includes zirconium together with conventional catalysts for the liquid phase oxidation of alkyl aromatics. A preferred catalyst system includes forms of zirconium, cobalt, manganese and bromine which are soluble in the oxidation solvent employed.

A surprising and unexpected feature of the present process is that the presence of relatively small amounts of zirconium drives the oxidation reaction towards completion and towards high yields of IBPA with minimal production of TMA, particularly when the process is practiced at relatively low temperatures and with relatively low molar ratios of bromine to the catalytically-active metals cobalt and manganese.

More specifically, the presently contemplated method for producing IBPA utilizes liquid phase oxidation of DXP and includes the steps of introducing into an oxidation reactor, or reaction zone, a DXP-containing admixture which is maintained in the reactor at an elevated temperature in the range of about 100° C. to about 240° C. (about 212° F. to about 464° F.), and preferably at autogenous pressure, for a time period sufficient to convert at least some of the introduced DXP to IBPA. The reaction admixture includes, in addition to DXP, an oxidation solvent that contains a $C_2$ to $C_6$ aliphatic acid, an oxygen-containing gas, and an oxidation catalyst system containing zirconium and additionally constituted by cobalt, manganese, and bromine, all in forms soluble in the aforementioned oxidation solvent. The oxidation solvent can also contain up to about 25 weight percent water on a total solvent basis, although the present particularly preferred oxidation solvent is a mixture comprised on a total solvent basis of about 95 weight percent acetic acid and about 5 weight percent water. An effluent stream having a reduced DXP content, but containing IBPA, is produced and is withdrawn from the reactor.

Either a batch or a continuous process scheme can be utilized in practicing the present invention.

The present process can be practiced efficiently and economically. Advantageously, existing equipment for carrying out the well-known Mid-Century alkyl aromatic oxidation process can be used so that capital costs for producing IBPA from DXP can be minimized so far as equipment considerations are concerned.

The catalyst employed oxidizes DXP to IBPA at relatively high conversion rates with minimum by-product (especially TMA) production.

Various other and further features, embodiments, and the like which are associated with the present invention will become apparent to those skilled in the art from the present description wherein presently preferred embodiments of the invention are illustrated by way of example. It is to be expressly understood, however, that the associated accompanying portions of this specification are provided for purposes of illustration and description only, and are not intended as limitations on the invention.

DETAILED DESCRIPTION OF PREFERRED EMBODIMENTS

In the practice of the process of the present invention, DXP is heated in a reaction zone under liquid phase conditions and in the presence of an oxidation catalyst. The following materials are charged to the reaction zone:

dixylylpropane,
oxidation solvent containing at least one aliphatic carboxylic acid having from 2 to 6 carbon atoms per molecule,
oxygen containing gas, such as air or oxygen, and
zirconium containing oxidation catalyst.

The oxidation solvent can optionally contain up to about 25 weight percent water on a total solvent weight basis. A present preference is to employ an oxidation composition comprised of a mixture of such an aliphatic acid and water wherein, on a 100 weight percent total composition basis, the quantity of aliphatic acid is in the range of about 99.5 to about 80 weight percent, and, correspondingly, the quantity of water is in the range of about 0.5 to about 20 weight percent. A present particularly preferred oxidation solvent is a mixture of about 95 weight percent acetic acid and about 5 weight percent water (total solvent weight basis).

The weight ratio of the oxidation solvent to the DXP in the reaction zone is preferably in the range of about 2:1 to about 10:1, and more preferably is in the range of about 2.5:1 to about 8:1. The amount of oxygen-containing gas charged to the reaction zone is preferably at least sufficient to achieve and maintain a molar excess of oxygen relative to the DXP present.

In addition to zirconium, the oxidation catalyst includes cobalt, manganese, and bromine components, all of which are soluble in the oxidation solvent. Preferably, these catalyst components are preliminarily dissolved in the solvent (or a portion of the solvent) before being charged to the reaction zone. The respective amounts of each of the components is chosen so that there are present in the reaction zone about 1 to about 50 milligram atoms of cobalt calculated as elemental cobalt per gram mole of DXP or about 0.05 to about 3 milligram atoms of cobalt per 100 parts by weight of the solution, about 0.1 to about 1 milligram atoms of manganese calculated as elemental manganese per milligram atom of cobalt calculated as elemental cobalt, about 0.01 to about 1 milligram atoms of zirconium calculated as elemental zirconium per milligram atom of cobalt calculated as elemental cobalt, and bromine in a bromine-to-(cobalt plus manganese) respective mole ratio of about 0.02 to about 1.

The use of zirconium in combination with the other catalyst components is believed to drive the oxidation reaction of DXP to completion, and thus to provide high yields of IBPA with minimum TMA production.

Examples of suitable aliphatic acids which may be employed as solvents in the practice of the process of this invention include acetic acid (presently preferred), propionic acid, n-butyric acid, isobutyric acid, n-valeric acid, trimethylacetic acid, caproic acid, and the like. Water can be, and typically is, present in the solvent.

Any convenient source of molecular oxygen may be employed for the oxidation process to this invention. Air is presently preferred as such source. The oxygen content of the molecular oxygen source can vary, for example, from that of the oxygen content of atmospheric air up to that of industrial grade oxygen and above.

The above indicated combination of materials is maintained in the reaction zone with agitation at a temperature in the range of about 100° C. to about 240° C. (about 212° F. to about 464° F.) and preferably about 140° C. to about 215° C. (about 284° F. to about 419° F.) while pressures are maintained in the reaction zone which are at least sufficient to maintain liquid phase conditions. These pressures are typically and conveniently autogenous pressures. Suitable reactor gauge pressures typically are in the range of about 10 kg/cm$^2$ to about 30 kg/cm$^2$, and can be as high as about 35 kg/cm$^2$. During the oxidation, the components in the reaction zone are stirred using an agitator means, such as conventional impellers, or the like. Such a temperature and such a pressure is preferably maintained for a time sufficient to oxidize at least about 75 mole percent of the charged dixylylpropane.

The process of the present invention can be practiced batchwise or continuously.

Preferably, the residence time of the components in the reaction zone at the particular elevated temperatures and pressures employed is sufficient to accomplish a conversion of at least about 85 weight percent of the DXP (based on charged weight of such starting compound). Typical and illustrative residence times needed to achieve such a conversion level are in the range of about 15 to about 60 minutes for inverse reaction temperatures in the range of about 220° C. to about 250° C. (about 428° F. to about 482° F.) although longer and shorter times can be used, depending upon variables such as temperature, catalyst concentration conversion desired, throughput ratio, available process equipment, and the like.

The yield of IBPA is more preferably greater than about 85 mole percent, based on starting DXP. In general, the amount of by-product TMA produced is characteristically less than about 4 mole percent, and, more preferably, is kept at less than about 2 mole percent, based on starting DXP.

The oxidation reaction of DXP to IBPA that is accomplished in the reaction zone proceeds relatively quickly. A substantial portion of the heat generated by the exothermic oxidation reaction is removed from the reaction mixture by vaporization of the solvent, and, to a smaller extent, of the DXP. The vaporized material and any unreacted oxygen and other gaseous components of, for example, an air feed to the reaction zone, pass preferably upwardly through the reaction zone and are withdrawn from the reaction zone above the level of the liquid reaction mixture in the reaction zone. The gaseous effluent from the reaction zone is passed through a reflux condenser, or the like, wherein the vaporized solvent and DXP are condensed for recycle or reuse. The non-condensable gases are conveniently vented.

Even under batch operating conditions, it is preferred to introduce oxygen-containing gas continuously into, and to withdraw gaseous effluent continuously from, an agitated reaction zone. This procedure is primarily done because it is desirable to maintain relatively high oxygen partial pressures in the reaction zone. Such excesses have the beneficial effect of reducing undesirable side reactions and also of favoring formation of the desired IBPA. It is presently more preferred that the oxygen-containing gas be fed to the reaction zone at a rate which results in an exhaust gas-vapor mixture containing about 1.8 to about 8 volume percent oxygen (measured on a solvent-free basis). Such an exhaust gas oxygen content is believed to be sufficient to provide in the reaction zone the desired level of oxygen concentration in the range of about 1.6 to about 2.8 moles of oxygen per methyl group of the DXP.

In general, a catalyst system used in the practice of the process of the present invention is provided by a combination of at least one solvent soluble zirconium compound together with solvent soluble catalyst components of the type heretofore conventionally used for liquid phase oxidation of alkyl aromatics, such as those comprised of a mixture of solvent soluble compounds of zirconium, cobalt, manganese and bromine.

For example, when a continuous process embodying this invention is contemplated, the feed stream(s) introduced into the reaction zone preferably contain(s) each of the DXP and catalyst system already dissolved in solvent. The weight ratio of the solvent containing dissolved catalyst and dissolved DXP fed into the reaction zone to the total amount of solvent introduced into the reaction zone is adjustable, but a present preference is to employ a ratio of solvent to dixylylpropane in the range of about 2.5:1 to about 8:1 in the reaction zone. If desired, the DXP and the catalyst can be introduced into the reaction zone separately from the solvent rather than being preliminarily dissolved in the solvent charged in a feed stream. A molar excess of oxygen relative to DXP is employed.

When the starting catalyst composition is comprised of dissolved forms of cobalt, manganese, zirconium, and bromine, it is presently preferred that the cobalt component calculated as elemental cobalt, be present in such solution at a level of about 0.05 to about 3 milligram atoms of cobalt per each 100 parts by weight of such solution. It is also preferred that the cobalt (calculated as elemental cobalt) be present in the range of about 1 to about 50 milligram atoms (mga) dissolved in the oxidation solvent per gram mole of the DXP; the manganese (calculated as elemental manganese) be present in the range of about 0.1 to about 10 mga dissolved in the oxidation solvent per milligram atom of cobalt (calculated as elemental cobalt); the zirconium (calculated as elemental zirconium) be present in the range from about 0.01 to about 1 mga dissolved in the oxidation solvent per milligram atom of cobalt; and the bromine (calculated as the elemental bromine ion) be present in the range of about 0.05 to about 2.5 mga dissolved in the oxidation solvent per milligram atom of cobalt. More preferably, and particularly in the case of practicing this invention with such a continuous process, these catalyst components are dissolved in the solvent in such respective indicated amounts with the mole ratio of bromine to total moles of cobalt and manganese present being in the range of about 0.02 to about 1.

When such a starting catalyst composition is being used in a system wherein the weight ratio of solvent employed to the amount of DXP charged is within the preferred range above indicated, the cobalt quantity present is preferably in the range of about 0.003 to about 0.17 weight percent (calculated as elemental cobalt) based on 100 weight percent combined cobalt and solvent with the respective amounts of manganese, zirconium, and bromine remaining as above defined in relation to cobalt.

In a preferred embodiment of the method of this invention, the preferred solvent is a mixture of acetic acid with water, such as above described, with each of the metals cobalt, manganese, and zirconium being provided in any of their known acetic acid-soluble ionic or combined forms. For example, the cobalt and manganese can each be introduced as the carbonate, the acetate tetrahydrate, and/or the bromide. The zirconium can likewise be introduced, if desired, as the carbonate, the acetate tetrahydrate, and/or the bromide. Zirconium can be added in any form that is soluble in the oxidation solvent. For example, $ZrO_2$ is commercially available from the Sheppard Chemical Company, Cincinnati, Ohio, as a solution in acetic acid, and such composition is very well suited for use in the practice of this invention.

Because of (1) the aforesaid requirements regarding the mole ratio of bromine to cobalt and manganese (each calculated as the elemental metal), and (2) the fact that the bromides of zirconium, cobalt and manganese inherently have a bromide to metal gram atom ratio of 2:1, the catalyst system used in this invention cannot be provided by the use of only bromides of zirconium, cobalt and manganese. Rather, the desired catalyst system is provided by selecting appropriate ratios of such bromide salts and other aliphatic carboxylic acid soluble salt forms (preferably acetate salt forms). The appropriate mga ratio (above indicated) of zirconium per gram mole of cobalt is likewise conveniently providable by the use of a combination of such carboxylic acid salts (acetates preferred) and bromide salts.

Suitable bromine sources include, for example, elemental bromine ($Br_2$), ionic bromide (for example, HBr, NaBr, KBr, and the like), or organic bromides, such as those which are known to provide bromide ions at the operating temperatures employed in the present liquid phase oxidation. Examples of such organic bromides include bromobenzenes, benzylbromide, mono-and dibromo acetic acid, bromoacetyl bromide, tetrabromoethane, ethylene-di-bromide, and the like. The total bromine content (consisting of the total molecular bromine and ionic bromide) in the solvent medium is used to provide the desired ratio of elemental bromine to total cobalt and manganese in the mga ratio indicated above. The quantity of bromide ion released from the organic bromides at the oxidation operating conditions can be readily determined by known analytical means. For example, tetrabromoethane, at typical operating temperatures in the range from about 172° C. to about 225° C. (about 339° F. to about 437° F.), has been found to yield in a reaction mixture such as above described about 3 gram atoms of bromine per gram mole of tetrabromoethane.

An illustrative and presently preferred resulting liquid effluent from the oxidation reaction zone comprises, on a 100 weight percent total basis, about 15 to about 25 weight percent IBPA, about 75 to about 85 weight percent total solvent comprised of water and aliphatic carboxylic acid (preferably aretic), about 0 to about 0.5 weight percent of unreacted DXP, about 0 05 to about 0.5 weight percent of oxidation catalyst components, about 0.1 to about 1 weight percent TMA, and from about 0.2 to about 2 weight percent of other reaction by-products. Other effluent compositions however, can be achieved without departing from the spirit and scope of the process of this invention.

In one presently preferred mode of practicing this invention, a staged temperature/pressure profile is used in a single batch reaction zone to control the rate of reaction, and to permit a higher final temperature to be used, so as to maximize IBPA production while minimizing the production of unwanted by-products, such as TMA. Such a staged batch procedure is also desirable because it minimizes the need for adjustments in the air feed rate, such as would otherwise be necessary in order to maintain a chosen minimum oxygen gas concentration in the vent gas stream, such as a level within the range hereinabove indicated. Thus, a starting reactant mixture:

having a solvent to DXP weight ratio of about 4:1 to 8:1;

where the solvent is comprised on a 100 weight percent total basis of about 80 to about 99.5 weight percent acetic acid, and, correspondingly, about 20 to about 0.5 weight percent water; and a zirconium-containing oxidation catalyst wherein the weight percent of cobalt dissolved in the solvent is in the range from about 0.02 to about 0.08; and the other catalyst components are present in amounts relative to the amount of cobalt present as hereinabove stated;

is maintained at a temperature in the range of about 154° C. to about 163° C. (about 310° F. to about 325° F.).

At this point, the first reaction stage commences as air is charged to the reactor (oxidation zone) at a feed rate which is conveniently about 20 SCFH per pound of DXP. As the temperature increases to about 166° C. to about 168° C., (about 330° F. to about 335° F.) the air feed rate is increased to a rate of about 80 to about 85 SCFH per pound of DXP, within a total time interval of preferably not more than about 2 to about 3 minutes. A vigorous reaction is then characteristically observed to occur over about the next 10 minutes. The reaction rate slows slightly over about the next succeeding 5 minutes thereafter. During this 15 to 20 minute approximate total time period, reactor pressures are adjusted to maintain the temperature within the indicated range of about 166° C. to about 168° C. (about 330° F. to about 335° F.). The oxygen level in the vent gas is maintained at about 2 to about 2.5 volume percent.

In a succeeding, or second, reaction phase, the reactor pressure is increased to elevate the reaction temperature to a range of about 201° C. to about 205° C. (about 395° F. to about 400° F.) over a time period of from about 20 to about 25 minutes, a presently preferred temperature increase rate being about 1.67° C. per minute (about 3° F. per minute). Typically, the reaction rate is maintained substantially constant for a time duration extending from the initiation of such second reaction phase for about 15 to about 30 minutes. During this period, the air feed rate is typically held constant in the range indicated with the vent oxygen level being maintained in the above indicated range of about 2 to about 2.5 volume percent, or about 80 to about 85 SCFH per pound of DXP.

However, during the next succeeding approximately 30 to 35 minute period, the reaction rate characteristically increases, and the air feed rate must then be increased to maintain the vent oxygen level from falling below about 2 volume percent. During this particular period, the air feed rate is typically increased to a maximum about 100 SCFH per pound of DXP.

Thereafter, the reaction rate starts to decrease inasmuch as a reactor pressure increase no longer increases the reaction zone temperature. The temperature may also begin to fall. At this point, the air feed rate is reduced to a level of about 50 SCFH per pound of DXP. Such reduction is accomplished over a time interval of about 2 to about 5 minutes. This feed rate scale down is desirable because it decreases the amount of undesirable by-products, such as diacid phthalide (DAP) and TMA, and increases the yield of desired IBPA. Thereafter, pressure and temperature reductions down to ambient can be conventionally accomplished.

In general, a reaction product removed from the oxidation reaction zone is further processed using conventional techniques to separate and to recover a purified IBPA. Alternatively, the IBPA can be first dehydrated to the corresponding IPAN, and the IPAN recovered.

The following examples are offered to specifically illustrate this invention. These examples are not to be construed as limiting the scope thereof, however.

EXAMPLE 1: EFFECT OF Zr/Co AND Br/(CO+MN) RATIO

To an agitator- and condenser-equipped pressurizable reactor vessel are charged batchwise:

TABLE I

| Starting Material Composition Initially Charged to Reactor | |
|---|---|
| Component | Weight Percent (100 weight percent total composition weight basis) |
| DXP | 13.0 |
| Acetic Acid | 82.4 |
| Water | 4.4 |
| Oxidation Catalyst | 0.2 |

The concentration of the cobalt catalyst component in the starting reactant mixture composition relative to DXP was about 6 milligram atoms of cobalt per gram mole of DXP, and the weight percent of cobalt based on 100 weight percent combined weight of total solvent plus cobalt was about 0.02 weight percent. The starting composition contained also about 1 milligram atom of manganese per milligram atom of cobalt, no zirconium, and bromine in a bromine to total cobalt-and-manganese mole ratio of about 1. The catalyst had the composition shown in Table II, below:

TABLE II

| Oxidation Catalyst Composition | |
|---|---|
| Component | Weight Percent (100 weight percent total catalyst weight basis) |
| Cobalt (acetate tetrahydrate) | 30.2 |
| Manganese (acetate tetrahydrate) | 30.2 |
| Bromine (HBr) (as 48% HBr in water) | 39.6 |
| Total Bromine | 22.3 |

This catalyst composition was preliminarily dissolved in a portion of the oxidation solvent, i.e., acetic acid and water, which was charged to the reactor initially. After the charging, pressurized air was continuously fed to the reactor at a rate of about 0.2 SCFM while the reactor was maintained at a temperature of about 177° C. and at an autogenous pressure corresponding to such temperature. The batch oxidation was continued for about 80 minutes.

Analysis of the batch liquid reaction product showed that the yield of IBPA was about 5.1 grams (equal to a conversion efficiency of about 5.7 mole percent based on starting DXP) while the yield of TMA was about 0.4 grams (equal to about 0.7 mole percent based on starting DXP).

The catalyst amounts, temperature, and results are summarized below in Table III, below, following Examples 2-4.

EXAMPLES 2-4: EFFECT OF Zr/Co AND Br(Co+Mn) RATIOS (CONTINUED)

The procedure of Example 1 was repeated a plurality of times, except that in each replication a different catalyst amount, and a different mole ratio of cobalt, manganese, zirconium, and bromine, were employed.

Table III below summarizes catalyst amounts as weight percent cobalt content based on solvent and as mole ratios of catalyst components expressed as Co:Mn:Zr:Br used in each replication. To achieve these respective mole ratios, the composition of the starting catalyst was varied from the catalyst composition shown above in Table II to provide the indicated catalyst component proportions. The reactor temperature, and the reaction yields in mole percent, are also shown in Table III.

The present Examples 1 to 4 illustrate the effects of changes in the cobalt/zirconium ratio and in the Br/(Co+Mn) ratio. In each pair of runs, identified in Table III as Example 1 and Example 2, and as Example 3 and Example 4, one run (Example 1 and Example 3, respectively) was made without the use of zirconium, and the other run (Example 2 and Example 4, respectively) with the use of zirconium. In each run where the zirconium was present, it was found that the addition of only a small amount of zirconium produces a tremendous and surprising increase in the IBPA yield. The effect is more pronounced in the Example 1/Example 2 pair because a lower overall catalyst loading was used.

Comparison of Example 2 with Example 4 provides an insight into the effect of the Br/(Co+Mn) ratio. Thus, in Example 4, higher temperatures and higher metals loadings were used than in Example 2. The yield value achieved in Example 2 is believed to be typical for a Mid-Century type oxidation process procedure as practiced in the prior art. These conditions were expected, based on prior art experience, to lead to the formation of more TMA. However, in Example 4, the TMA yield is unexpectedly much lower than that in Example 2. It is believed that this is because of the very low molar Br/(Co+Mn) ratio of 0.1 used in Example 4, as opposed to the ratio of 1.0 used in Example 2.

TABLE III

| Effects of Varying Catalyst Concentration and Components | | | | |
|---|---|---|---|---|
| | Ex. 1 | Ex. 2 | Ex. 3 | Ex. 4 |
| Variable | | | | |
| Temperature °F. | 350 | 350 | 385 | 385 |
| (°C.) | (177) | (177) | (196) | (196) |
| Wt % Co on total solvent | 0.02 | 0.02 | 0.08 | 0.08 |
| Co:Mn:Zr:Br (molar ratio) | 1:1:0:2 | 1:1:0.1:2 | 1:2:0:1 | 1:2:0.1:0.3 |
| Solvent: DXP weight ratio | 7:1 | 7:1 | 7:1 | 7:1 |
| Reaction Yields mole % | | | | |
| IBPA | 5.7 | 82.8 | 66.1 | 86.9 |
| TMA | 0.7 | 7.3 | 2.4 | 3.7 |

EXAMPLES 5-7: TEMPERATURE EFFECT ON OXIDATION

The procedure of Example 1 was repeated except that different catalyst amounts and different mole ratios of cobalt, manganese, zirconium, and bromine were employed in each of various starting mixtures. TABLE IV, below, summarizes the catalyst amounts (expressed as weight percent of cobalt content based on total amount of solvent and cobalt weight) and mole ratios of catalyst components (expressed as Co:Mn:Zr:Br). To achieve these respective mole ratios for each Example, the composition of the starting catalyst was adjusted from the composition shown in Example 1.

As TABLE IV below shows, the amount of TMA produced increases as the reaction temperature increases.

TABLE IV

| Effect of Temperature in Batch DXP Oxidations | | | |
|---|---|---|---|
| | Run | | |
| | A | B | C |
| Variable | | | |
| Temperature °F. | 385 | 350 | 310 |
| (°C.) | (196) | (177) | (149) |
| Wt % Co on | 0.08 | 0.08 | 0.08 |

TABLE IV-continued

| Effect of Temperature in Batch DXP Oxidations | | | |
|---|---|---|---|
| | Run | | |
| | A | B | C |
| total solvent | | | |
| Co:Mn:Zr:Br (molar ratio) | 1:2:0.1:0.3 | 1:2:0.1:0.3 | 1:2:0.1:0.3 |
| Solvent:DXP (weight ratio) | 7:1 | 7:1 | 7:1 |
| Run Time (min.) | 31 | 31 | 52 |
| Reactor Yields (mole %) | | | |
| IBPA | 85.3 | 86.3 | 75.6 |
| TMA | 3.7 | 2.3 | 1.1 |

EXAMPLE 8: EVALUATION

The procedure of Example 1 was repeated except that the reactor temperature employed was 350° F. (171° C.), the weight percent of cobalt based on solvent was 0.08, the molar ratio of Co:Mn:Zr:Br was 1:2:0.1:0.3, and the solvent/DXP weight ratio was 7:1. Using these conditions, a set of 20 batch oxidations of DXP to IBPA were performed in five groups consisting of an average of four runs each.

The results are summarized in TABLE V, below. Specifically, TABLE V contains the results from each of the five groups, along with the overall mean and standard deviation for each.

These results confirm that a batch oxidation process of the present invention employing a catalyst of zirconium, cobalt, manganese and bromine and utilizing a relatively low temperature and a relatively low Br/(Co+Mn) mole ratio produces a relatively high yield of IBPA with only a relatively small amount of TMA.

TABLE V

| Results from Multiple IBPA Production Batches | | | | | | |
|---|---|---|---|---|---|---|
| Product Component | Yield for Run No., mol % | | | | | Mean ± Std. Dev. for All Runs |
| | 1 | 2 | 3 | 4 | 5 | |
| IBPA | 93.5 | 91.8 | 86.5 | 86.1 | 86.6 | 88.9 ± 3.5 |
| TMA | 3.0 | 3.0 | 3.3 | 3.3 | 3.7 | 3.3 ± 0.3 |

EXAMPLE 9: STAGED BATCH PROCESS

DXP was oxidized to IBPA in a batch reactor using a solvent-to-DXP weight ratio of about 6.75:1 where the solvent initially comprised, on a 100 weight percent solvent basis, about 95 weight percent acetic acid and about 5 weight percent water.

The solvent contained about 0.03 weight percent of dissolved cobalt (calculated as elemental cobalt), and the molar ratio of dissolved catalyst components with respect to cobalt, expressed as Co:Mn:Zr:Br, was 1.:2.:0.06:0.3. The catalyst concentration was relatively low in order to minimize the initial reaction rate. A very low molar Br/(Co+Mn) ratio of about 0.1 was used to minimize TMA formation and to slow down the initial rate of reaction. The presence of a small amount of zirconium minimized the amount of oxidation intermediates formed and drove the reaction to completion.

In a first reaction stage, the DXP, solvent and catalyst were heated with agitation to about 320° F. (about 160° C.) and air was then charged continuously commencing at a rate of about 20 SCFH per pound of DXP. The temperature was increased over a time period of about 3 minutes to about 330° F. (about 166° C. and held at this level for about 15 minutes. As the temperature was thus being increased, the air feed rate was increased to about 83 SCFH per pound of DXP and was held at this level. Over about the first 10 minutes, the reaction was observed to be very vigorous, after which time interval the reaction rate slowed slightly over the next approximately 5-minute period. Throughout this time period, the reactor pressure was adjusted to maintain 330° F. (166° C.). The vent $O_2$ level was in the range of about 2 to about 2.5 volume percent.

In the second reaction stage, which began at about 15 minutes after oxidation was initiated, the pressure was ramped (continuously increased) to elevate the reaction temperature from about 330° F. (about 166° C.) to about 395° F. to about 400° F. (about 201° C. to about 204° C.) over a time period of about 22 minutes at the approximate rate of about 3° F./minute (1.67° C./min.). A temperature in this range served to hold the reaction rate substantially constant during the next time period of about 15 to about 30 minutes after its initiation. During this period the air feed rate was held constant with the vent $O_2$ level being in the range indicated. However, during the next approximately 30 to 35 minute time period thereafter, the reaction rate increased, and the air feed rate was increased to a maximum of about 100 SCFH per pound of DXP to prevent the vent gas $O_2$ level from falling below 2 percent.

The start of the next or third reaction stage was marked by the point at which the reaction rate decreased as shown by the fact that upon increasing the reactor pressure the reaction temperature did not increase. At this point, the air feed rate was reduced over about a 2 to 5 minute period. Such action decreased the quantity of the unwanted by-product diacid phthalide (DAP) intermediate produced and also of unwanted TMA produced. Thereafter, heating was terminated, air feed was halted, and the reactor was depressurized. Optionally, solvent withdrawal by distillation can be used to reduce to weight of the total reactor effluent.

The IBPA yield was about 89 to 90 mole percent, TMA yield was about 4.5 to 5.5 mole percent, and the maximum DAP yield was about 0.8 to 1 percent that of IBPA.

Although the present invention has been described and illustrated based on the presently available information and embodiments, it is to be understood that modifications and variations are within the spirit and scope of the invention, as those skilled in the art will readily appreciate and that such are within the purview and scope of the appended claims.

I claim:

1. A method for producing isopropylidene bis(phthalic acid) by the liquid phase oxidation of dixylylpropane which comprises the steps of:

introducing into an oxidation reactor dixylylpropane, an oxidation solvent containing an aliphatic acid having 2 to 6 carbon atoms per molecule, an oxygen-containing gas, and a zirconium-containing oxidation catalyst system soluble in said oxidation solvent and additionally constituted by cobalt, manganese, and bromine;

agitating the resulting reactor contents to produce an admixture;

maintaining the produced admixture in said reactor at a temperature in the range of about 100° C. to about 240° C. and at autogenous elevated pressure for a time period to produce a reaction mixture enriched in isopropylidene bis(phthalic acid); and withdrawing from said reactor an effluent stream having a relatively lower dixylylpropane content than said admixture and containing isopropylidene bis(phthalic acid).

2. The method of claim 1 wherein the weight ratio of said solvent to said dixylylpropane is in the range of about 2:1 to about 10:1.

3. The method of claim 2 wherein said catalyst is characterized by:

about 1 to about 50 milligram atoms of cobalt, calculated as elemental cobalt, dissolved in said solvent per gram mole of said dixylylpropane, about 0.1 to about 10 milligram atoms of manganese calculated as elemental manganese dissolved in said solvent per milligram atom of said cobalt, bout 0.01 to about 1 milligram atoms of zirconium calculated as elemental zirconium dissolved in said solvent per milligram atom of said cobalt, and about 0.05 to about 2.5 milligram atoms of bromine calculated as elemental bromine dissolved in said solvent per milligram atom of said cobalt.

4. A method for producing isopropylidene bis(phthalic acid) from dixylylpropane comprising reacting under liquid phase conditions dixylylpropane with an oxygen containing gas in an aqueous oxidation solvent containing an aliphatic carboxylic acid having 2 to 6 carbon atoms per molecule at a temperature in the range of about 100° C. to about 240° C. and at an elevated pressure in the presence of an oxidation catalyst, while maintaining:

a molar excess of oxygen relative to said dixylylpropane, a weight ratio of said solvent to said dixylylpropane in the range of about 2:1 to about 10:1, said oxidation catalyst comprising cobalt, manganese, zirconium, and bromine components which are each dissolved in said solvent, there being present:

about 1 to about 50 milligram atoms of cobalt per gram mole of said dixylylpropane, about 0.1 to about 10 milligram atoms of manganese per milligram atom of cobalt, about 0.01 to about 1 milligram atoms of zirconium per milligram atom of cobalt, and bromine in a bromine-to-(cobalt plus manganese) mole ratio of about 0.02 to about 1.

5. A method for producing isopxopylidene bis(phthalic acid) comprising the steps of (A) charging to a reaction zone each of (1) dixylylpropane, (2) solvent comprising on a 100 weight percent basis about 0.5 to about 20 weight percent of water and about 80 to about 99.5 weight percent of at least one aliphatic carboxylic acid having from 2 to 6 carbon atoms per molecule, the weight ratio of said solvent to said dixylylpropane being in the range from about 2:1 to 10:1, (3) oxygen in an amount sufficient to produce a molar excess of oxygen to said dixylylpropane, and (4) an oxidation catalyst comprising cobalt, manganese, zirconium, and bromine components which are each dissolved in said solvent, there being present:

about 1 to about 50 milligram atoms of cobalt per gram mole of said dixylylpropane, about 0.1 to about 10 milligram atoms of manganese per milligram atom of cobalt, about 0.01 to about 1.0 milligram atoms of zirconium per milligram atom of cobalt, and the bromine being present in a bromine-to-(cobalt plus manganese) mole ratio of about 0.02 to about 1, (B) maintaining the resulting mixture in said reaction zone under autogeneous pressure and at a temperature in the range of about 100° C. to about 240° C. for a time period sufficient to oxidize at least about 75 mole percent of the charged dixylylpropane while agitating said mixture, and (c) removing from said reaction zone the resulting product mixture.

6. The process of claim 5 wherein said steps are practiced batchwise.

7. The process of claim 5 wherein said steps are practiced continuously.

8. The process of claim 5 wherein reaction is maintained until the yield of said isopropylidene bis(phthalic acid) is greater than about 85 mole percent based on starting dixylylpropane.

9. The process of claim 5 wherein said aliphatic carboxylic acid is acetic acid.

10. The process of claim 5 wherein said oxygen is supplied to said reaction zone as air, and, during said oxidation, said air is continuously supplied to said reaction zone at a feed rate which is sufficient to provide in said reaction zone oxygen in an amount of about 1.6 to about 2.8 moles per methyl group of said dixylylpropane present.

11. The process of claim 5 wherein the solvent-to-dixylylpropane weight ratio is about 2.5:1 to about 8:1.

* * * * *

UNITED STATES PATENT AND TRADEMARK OFFICE
CERTIFICATE OF CORRECTION

PATENT NO. : 5,028,737
DATED : July 2, 1991
INVENTOR(S) : Paul A. Sanchez

It is certified that error appears in the above-indentified patent and that said Letters Patent is hereby corrected as shown below:

Column 6, line 38 ",about 005 to" should read --about 0.05 to--

Column 12, line 49, "isopxopylidene" should read --isopropylidene--

Signed and Sealed this

Twenty-second Day of February, 1994

Attest:

BRUCE LEHMAN

*Attesting Officer*         *Commissioner of Patents and Trademarks*